United States Patent [19]

Templeton et al.

[11] Patent Number: 5,291,341
[45] Date of Patent: Mar. 1, 1994

[54] LASER ATTENUATION DEVICE WITH SACRIFICIAL MIRROR

[75] Inventors: Douglas W. Templeton, Macomb County, Mich.; C. H. Chen, Knox County; Ronald C. Phillips, Roane County, both of Tenn.

[73] Assignee: The United States of America as represented by the Secretary of the Army, Washington, D.C.

[21] Appl. No.: 83,221

[22] Filed: Jun. 29, 1993

[51] Int. Cl.$^5$ .......................... G02B 17/00; G02F 1/01
[52] U.S. Cl. ....................... 359/884; 359/297; 359/359
[58] Field of Search ............... 359/884, 297, 359, 634

[56] References Cited

U.S. PATENT DOCUMENTS

| | | | |
|---|---|---|---|
| 3,734,592 | 5/1973 | Sztankay et al. | 359/297 |
| 3,982,206 | 9/1976 | Poulsen | 359/297 |
| 4,719,342 | 1/1988 | Cohn et al. | 359/297 |
| 4,917,481 | 4/1990 | Koechner | 359/292 |

*Primary Examiner*—Eugene R. LaRoche
*Assistant Examiner*—Tan Nguyen
*Attorney, Agent, or Firm*—Peter A. Taucher; Gail S. Soderling

[57] ABSTRACT

An eye protection device for protection against a broad spectrum of incident high intensity radiation includes a beam splitter which transmits the radiation to a first focusing lens which in turn focuses the radiation on a first mirror. The first mirror has a sacrificial surface which desorbs if the radiation has a predetermined minimum intensity. A second lens receives radiation reflected from the first mirror and directs the beam orthogonally onto a second mirror. The beam reflects off the second mirror and is directed back through the second lens which refocuses the beam onto the surface of the first mirror at the original area. When the initial beam was above the minimum, reflectivity at this location will have been destroyed and the beam will pass harmlessly through the mirror. If the initial beam does not destroy the surface, the beam will be reflected back to the beam splitter and then to a receiving device.

3 Claims, 1 Drawing Sheet

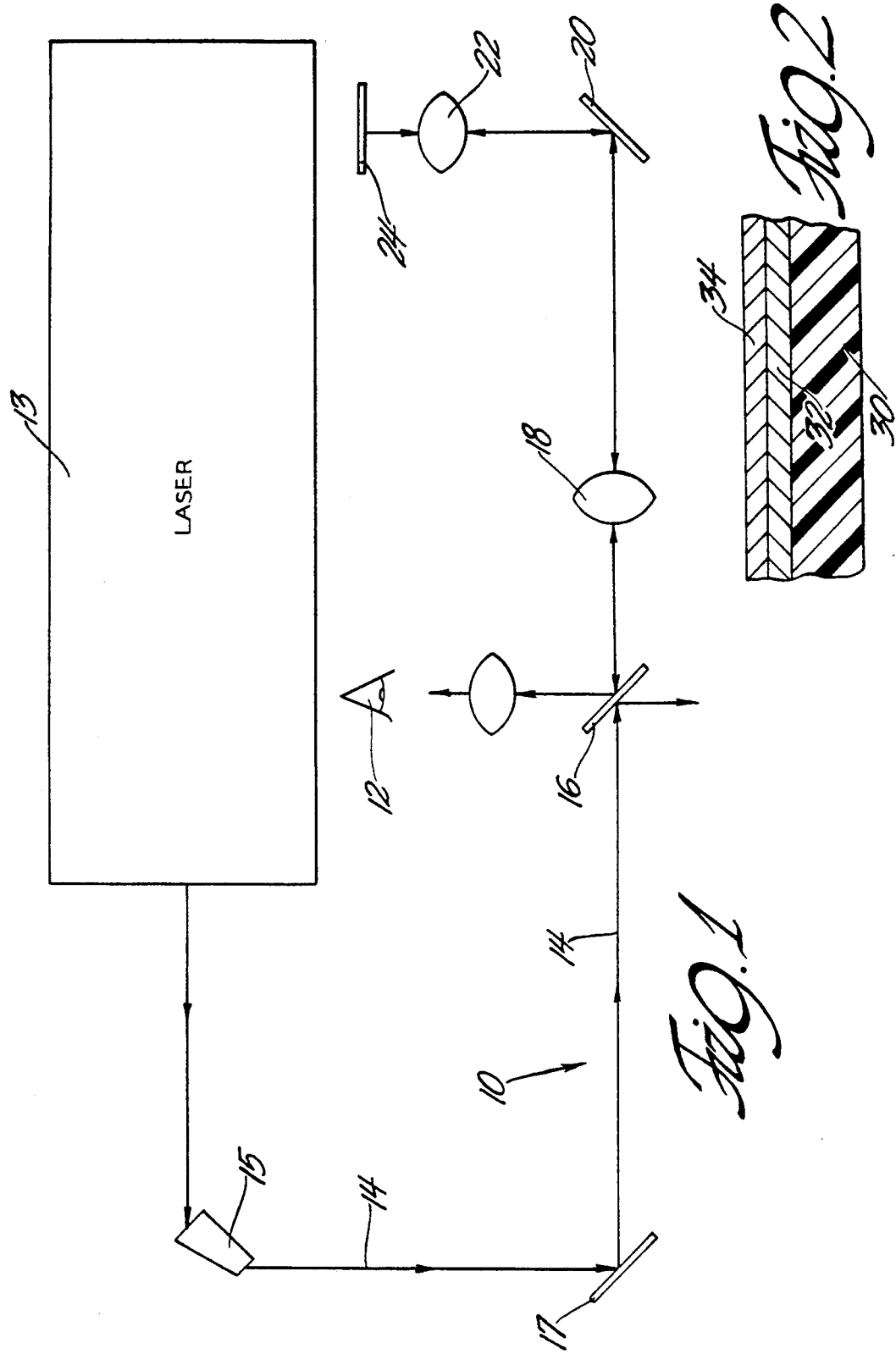

LASER ATTENUATION DEVICE WITH SACRIFICIAL MIRROR

GOVERNMENT INTEREST

The invention described herein may be manufactured, used and licensed by or for the Government for governmental purposes without payment to me of any royalty.

BACKGROUND OF THE INVENTION

1. Field of the Invention

In one aspect this invention relates to eye protection for combat personnel. In yet a further aspect, this invention relates to methods of absorbing light beams.

2. Prior Art

Laser technology has become an increasingly important part of modern technological warfare. Lasers are used in aiming devices, range finders, and as countermeasures to defeat various optical aiming and ranging devices.

As part of the development of laser technology, tuneable dye lasers are being developed which operate by pumping from other lasers or flash lamps. Such lasers provide high energy pulses and can be made in large variety of different wave lengths. The TI-Sapphire lasers now being developed can also provide high repetitions of tuneable energy. This means the exact wave length used by an opponent can not be known in advance requiring that any acceptable protection device be useful over a broad spectrum.

Thus, battlefield personnel are in danger of being exposed to laser radiation of an unknown frequency either casually or intentionally. With the power densities available from today's laser technology, serious damage will be done to unprotected eyes and also the optical devices used on combat vehicles. The radiation comes in discrete bursts of ebergy ranging from a few microjoules up to several joules in intensity and for periods of time from a few nanoseconds to a few microseconds.

To prevent eye damage, any light absorption device must react quickly, on the order of less than 10 picoseconds and absorb light in the range of 400 to 700 nm. Because of the limited time to react, the device must operate passively. A further constraint is the device must transmit light of normal intensity so the user can function in normal light conditions while the bursts of high intensity are prevented from reaching the users eye. This implies that the absorption material operates in a nonlinear manner or initiates protection at some predetermined minimum beam power.

Indirect viewing means which protect a viewer have been developed. One such class of viewers includes a system where the incoming light signal is amplified until all signal are equal in strength and then the modified light beam is attenuated to a safe level. These devices are large and bulky, and also require an external power source making them unsuitable for battlefield application. Particularly with respect to viewers carried by personnel.

Attempts have been made to develop goggles which are suitable for attenuating incoming laser beams during the last several years. The attenuation must be to a power level of about 1 $\mu j$ which represents an attenuation factor of at least 10,000 since the available lasers can deliver up to several joules of power in the beam with little beam divergence. Partial solutions for beams at a preselected wave length have been achieved; however, there presently exist no protective systems for personnel and equipment which are passive, can react to a broad spectrum of high intensity beams, and simultaneously allow the user to function under normal light conditions.

BRIEF SUMMARY OF THE INVENTION

The problems of the prior art are overcome by the present invention which comprises an eye protection device adapted to protect against a broad spectrum of incident high intensity radiation while allowing the transmission of normal radiation levels. The system includes a beam splitter which receives the initial beam and transmits a substantial portion of the incident radiation to a first focusing lens placed on the side of the beam splitter opposite the source of the incident beam.

The first lens receives and focuses the radiation to a narrowly defined focusing area which intensifies the incident beam. A first mirror is placed at the focusing area so as to receive and reflect the focused beam from the first lens.

The surface of the first mirror is designed so that if the initial incident radiation has an intensity of at least 25 millijoules, the focused beam will cause a localized heating at the focusing area on the mirror surface, raising the temperature to the vaporization temperature of the reflective surface.

A second lens is placed to receive any radiation reflected from the first mirror and recollimate the light directing the recollimated beam orthogonally onto the reflective surface of a second mirror. Any radiation in the recollimated beam reflects off the second mirror and is then directed back through the second lens which refocuses the beam onto the surface of the first mirror at the area originally heated by the beam.

If the initial beam was above the threshold power level, the reflectivity of the surface at this location will have been destroyed by the vaporization of the surface due to the initial heating of the beam and the beam will pass harmlessly through the mirror. But, if the initial beam was not powerful enough to destroy the surface, the beam will be reflected off the first mirror, through the first lens and onto the side of the beam splitter facing the first lens which will direct the beam to a receiving device.

BRIEF DESCRIPTION OF THE DRAWING

In the accompanying drawing:

FIG. 1 represents a schematic of one structure according to this invention; and

FIG. 2 is a side view, in section, of a mirror construction useful in the practice of this invention.

DETAILED DESCRIPTION OF PREFERRED EMBODIMENTS

Referring to the accompanying drawing and initially to FIG. 1, an eye protection device according to this invention designated generally 10 is paced within an optical system (not shown) but which could be a hand held device carried by personnel such as an optical range finder. Such devices are used for direct observation by troops and the users eye 12, sensitive to large radiation doses receives the incoming beam. For the purposes of discussion, the laser beam is generated by a YAG laser 13 and the laser beam directed into a prism 15 which in turn directs the beam onto a standard mirror 17. The resulting beam is representative of the types of beams encountered under battlefield conditions.

As shown, the incident beam 14 first contacts a beam splitter 16. The beam splitter 16 receives and transmits a substantial portion of the incident radiation to a first focusing lens 18 placed on the side of the beam splitter opposite the beam source.

The first focusing lens 18 receives and focuses the beam into a narrowly defined focusing area at the surface of a first mirror 20. The focused beam is reflected by the first mirror 20 towards a second lens 22. The focused beam from lens 18 will cause a localized heating of the first mirror's surface in the focused area. If the initial incident radiation has an intensity of about 0.01 to 10 mJ/sq cm the beam will heat the focusing area to the vaporization temperature of the mirror's reflective surface.

Because the heating and vaporization of the first mirrors surface are not instantaneous, and incident waves will normally have a square wave function, the initial portion of the beam will reflect off the first mirror 20 and be directed into the second lens 22.

The second lens 22 will receive and recollimate the beam which will strike a second mirror 24 orthogonally. The second mirror 24 reflects the recollimated beam back through the second lens 22 which refocuses the beam onto the surface of the first mirror at the original focusing area heated by the beam. If the initial beam was above the threshold power level, the reflectivity of the surface of the first mirror 20 at this location will have been destroyed by the vaporization of the surface caused by the initial heating of the beam and the beam will pass harmlessly into the first mirror 20.

As the surface of the first mirror 20 is vaporized, the resulting vapor caused by desorbtion of the metal film will move away at a speed of about $10^6$ cm/sec. The vapor must move away from the first mirror's surface by at least a fraction of a wave length to significantly reduce the surface's reflectivity. A displacement of about 50 nm or more will provide the required decrease in reflectivity. About 5 picoseconds will be needed for the desorbed metal to move at least 50 nm at a velocity of $10^6$ cm/sec. Thus the system's construction should provide for a time delay from the first reflection off the first mirror 20 until the beam returns from the second mirror 24 of about 5 picoseconds.

When the initial beam is at normal levels, the first mirror's surface will be unaffected and the beam returning from the second mirror 24 will be reflected off the first mirror 20, through the first lens and onto the side of the beam splitter 16 facing the first lens. The beam splitter 16 is positioned so as to direct the returning beam to a receiving device shown as an eye 12.

The present invention is designed to allow the manufacture of a light weight system at a reasonable price. One key to a workable system is a light weight mirror. One suggested system for a light weight mirror is shown in FIG. 2. In this figure, a plastic backing 30 is coated with a reflective layer of metallic material. As shown the metallic coating has two layers 32, 34. The base layer 32 would normally be aluminum or other similar low vaporization temperature metal over coated with a thin highly reflective layer such as gold. It has been observed experimentally that mirrors with a gold layer over the aluminum will have larger damage areas when the incident beam meets the threshold power criteria which produces a better beam attenuation.

The plastic can be chosen from a class of plastics which can be metallized one example being mylar. Mylar is a commonly available plastic which is coated with shiny metal films using conventional metallizing techniques. These techniques are well known and a detailed description is omitted in the interest of brevity.

EXAMPLE

To test various parameters an experimental device corresponding in construction to FIG. 1 was constructed. A Quanta Ray DCR Nd: YAG multimode Q-switched laser with a beam divergence of 0.5 mrad was used for a beam source. The laser can deliver pulse length of 7 nanoseconds and the frequency was doubled to produce 532 nm light. The Q-switch was activated once every five seconds with the laser cavity oscillation at 10 Hz.

Power measurements were performed using a Coherent 210 power meter while the laser operated at 10 Hz. Power reflecting off mirrors was measured using Gentec ED-100A Joulemeter connected to a Tektronix oscilloscope. The laser beam was passed through a Pellin Boca prism and reflected onto the beam splitter with a standard mirror.

The incident laser beam was passed through a beam splitter and into a 2.5 cm diameter and 20 cm focal length lens which focused the beam on to a mylar backed aluminized mirror. One mirror tested was a clear mylar backing coated with 100 nm of aluminum. A second type of mirror tested was a material available from National Photocolor Corp which comprised a 2.5 micron black mylar film with 500 Angstroms of Aluminum coating. The undamaged reflectivity of these mirrors was on the order of 80% of the incident energy.

Light reflecting off the first mirror passed into a second 2.5 cm diameter 20 cm focal length lens after which the beam impinged perpendicularly on a normal glass mirror. The light was reflected back to the second lens and was in turn refocused on to the first mirror at the same spot as the beam originally struck the first mirror. Thus if the incident beam destroyed the mirror's surface, the beam was not reflected back to the beam splitter and was attenuated.

After each shot of the laser the first mirror was moved so there would be an undamaged spot for the beam to strike.

At an incident beam intensity of 40 mJ a damaged area about 1 cm in diameter was formed on the first mirror's surface due to desorbtion of the aluminum coating. The reflected light from the damaged spot measured by a detector near the beam splitter was less than 1 μJ representing an attenuation factor of more than 40,000.

Various modifications and alterations will become apparent to those skilled in the art without departing from the scope and spirit of this invention and it is understood that this invention is not limited to the illustrative embodiments set forth above.

What is claimed is:

1. An eye protection device adapted to protect against a broad spectrum of incident high intensity radiation while allowing the transmission of normal radiation levels, including: a beam splitter which transmits a substantial portion of the incident radiation beam; a focusing lens placed on the side of the beam splitter opposite the source of the incident radiation beam, the lens receiving and focusing the incident radiation beam to a narrowly defined focusing area to further intensify the incident radiation beam; a first mirror placed and adapted to receive the focused incident radiation from the first lens, the surface of the mirror being sufficiently absorptive of incident radiation that a focused incident beam with an initial intensity of at least 25 millijoules will cause a heating of the mirror surface to the vaporization temperature of the reflective surface of the mirror at the point of the focused beam; a second lens placed to receive radiation reflected from the first mirror and recollimates the light onto a reflective surface of a second mirror the recollimated beam reflecting off the second mirror is then reflected back through the second lens which refocuses the beam onto the sacrificial surface of the first mirror at the area originally heated by the beam, if the initial beam was above the threshold, the reflectivity of the surface at this location will have been destroyed by the initial heating of the beam and the beam will pass through the mirror but if the beam was not sufficient to destroy the surface, the beam will be reflected off the first mirror, through the first lens and onto and the side of the beam splitter facing the first lens which passes the beam to the receiving device.

2. The system of claim 1, where the first mirror is an aluminum surfaced plastic material.

3. The system of claim 2, where the mirror surface is a multilayered construction of a gold coating over an aluminum surface on the plastic material.

* * * * *